United States Patent
Steyn

(10) Patent No.: US 8,460,246 B2
(45) Date of Patent: Jun. 11, 2013

(54) PROTECTIVE DEVICE FOR A NEEDLE ASSEMBLY

(76) Inventor: Ricardo Sheath Oxford Steyn, Randpark Ridge (ZA)

( * ) Notice: Subject to any disclaimer, the term of this patent is extended or adjusted under 35 U.S.C. 154(b) by 575 days.

(21) Appl. No.: 12/531,153

(22) PCT Filed: Mar. 14, 2007

(86) PCT No.: PCT/IB2007/000620
§ 371 (c)(1),
(2), (4) Date: Dec. 29, 2009

(87) PCT Pub. No.: WO2007/141603
PCT Pub. Date: Dec. 13, 2007

(65) Prior Publication Data
US 2010/0114036 A1    May 6, 2010

(51) Int. Cl.
*A61M 5/178* (2006.01)
(52) U.S. Cl.
USPC .................. 604/164.08; 604/192; 604/263
(58) Field of Classification Search
USPC ................................ 604/164.08, 192, 263
See application file for complete search history.

(56) References Cited

U.S. PATENT DOCUMENTS

| | | | | |
|---|---|---|---|---|
| 5,256,152 | A | * | 10/1993 | Marks .......................... 604/198 |
| 5,746,718 | A | * | 5/1998 | Steyn ............................ 604/192 |
| 7,449,012 | B2 | * | 11/2008 | Young et al. .................. 604/192 |
| 2003/0181872 | A1 | | 9/2003 | Newby |
| 2003/0216687 | A1 | | 11/2003 | Hwang |

FOREIGN PATENT DOCUMENTS

WO    2006/032064 A1    3/2006

OTHER PUBLICATIONS

International Search Report for PCT/IB2007/000620 Dated Dec. 14, 2007.

* cited by examiner

*Primary Examiner* — Kevin C Sirmons
*Assistant Examiner* — Deanna K Hall
(74) *Attorney, Agent, or Firm* — Nixon Peabody LLP; Jeffrey L. Costellia

(57) ABSTRACT

The invention provides a protective device (10) for a needle assembly (12) having a needle hub (14) and a needle (16) projecting from the hub. The protective device includes an end cap (20) which has an opening (36) through which the needle (16) may pass, and a resilient member (22) extending about the needle (16) between the needle hub (14) and the end cap (20). The resilient member (22) is deformable between a first condition in which it holds the end cap (20) over a sharpened end (18) of the needle (16) and a second condition in which the end cap (20) is withdrawn from the sharpened end of the needle (16). Furthermore, the resilient member (22) is biased towards the first condition and is arranged to bias the end cap (20) into a safety position in which the sharpened end of the needle (16) is offset relative to the opening (36) in the end cap (20). The protective device (10) also includes a sheath (24) covering at least the sharpened end (18) of the needle (16). The sheath (24) extends into the opening (36) in the end cap (20) so as to hold the sharpened end of the needle (16) in alignment with the opening (36), against the bias of the end cap (20). The sheath (24) is also removable from the needle (16) to expose the sharpened end (18) for use, and after use, to allow the resilient member (22), upon return to the first condition, to automatically displace the end cap (20) into the safety position.

17 Claims, 2 Drawing Sheets

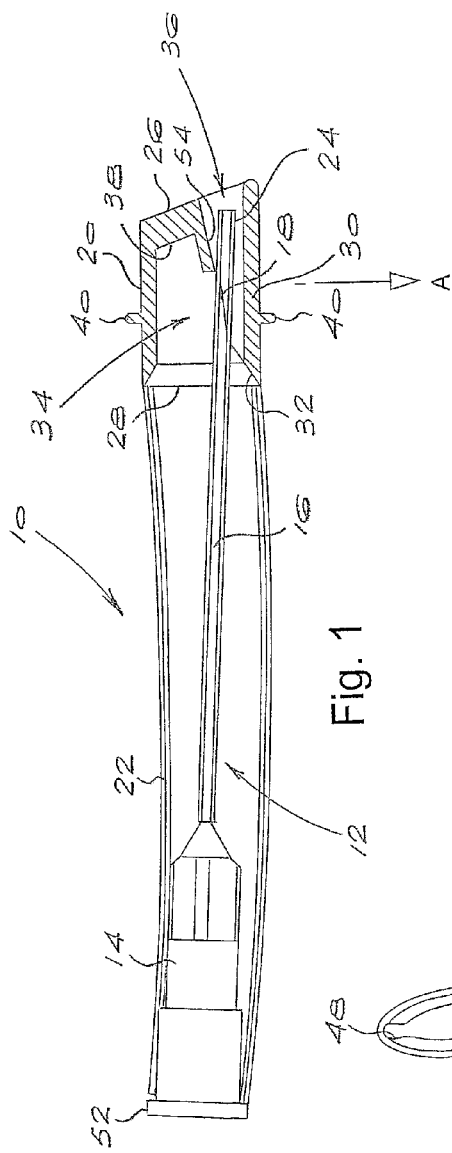
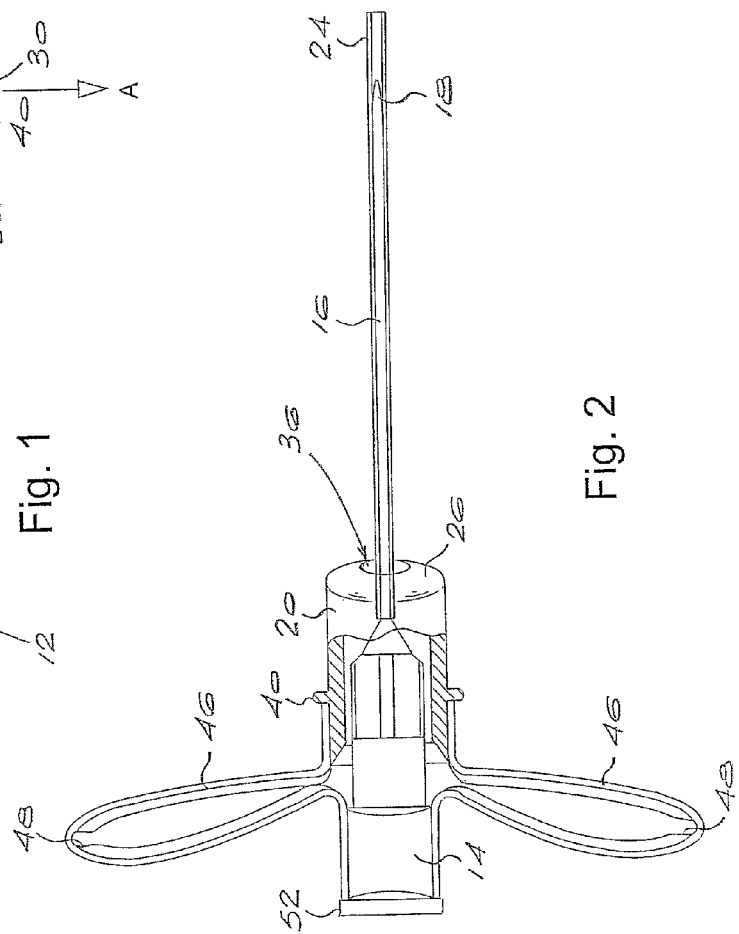

PROTECTIVE DEVICE FOR A NEEDLE ASSEMBLY

BACKGROUND OF THE INVENTION

THIS invention relates to medical equipment, and more specifically to a protective device for a needle assembly having a hub for attachment to a syringe, a catheter or a blood-drawing holder, and a hypodermic needle extending from the hub.

Protective devices for needle assemblies are known. For example, U.S. Pat. No. 5,538,508 discloses a protective device which includes an end cap and a resilient, generally tubular member for holding the end cap over a sharpened end of a hypodermic needle. The end cap includes a blocking surface for containing the sharpened end of the needle, and an off-centre opening adjacent the blocking surface for allowing the needle to pass through the end cap for use. The generally tubular member is arranged to bias the end cap into a safe position in which the sharpened end of the needle is aligned with the blocking surface. To expose the needle for use, it is necessary to manipulate the end cap by aligning the sharpened end of the needle with the opening in the end cap and then withdrawing the end cap over the needle against the resilience of the generally tubular member.

Although this device is effective in containing the sharpened end of the needle before and after use, aligning the needle with the opening in the end cap and also then overcoming the resiliency of the generally tubular member can be awkward in certain medical applications.

It is an object of the present invention to provide a protective device for a needle assembly which is effective in containing the sharpened end of a needle before and after use, and which allows the needle to be exposed for use relatively easily.

SUMMARY OF THE INVENTION

According to the invention there is provided a protective device for a needle assembly having a needle hub and a needle projecting from the hub, the protective device comprising:
  an end cap which includes an opening through which the needle may pass;
  a resilient member extending about the needle between the needle hub and the end cap, the resilient member being deformable between a first condition in which it holds the end cap over a sharpened end of the needle and a second condition in which the end cap is withdrawn from the sharpened end of the needle, the resilient member being biased towards the first condition and being arranged to bias the end cap into a safety position in which the sharpened end of the needle is offset relative to the opening in the end cap; and
  a sheath covering at least the sharpened end of the needle, the sheath extending into or through the opening in the end cap so as to hold the sharpened end of the needle in alignment with the opening, against the bias of the end cap, and the sheath being removable from the needle to expose the sharpened end for use, and after use, to allow the resilient member, upon return to the first condition, to automatically displace the end cap into the safety position.

Preferably, the sheath is formed from a rigid material which extends over the sharpened end of the needle.

In one arrangement, the sheath comprises a sleeve which extends over the sharpened end of the needle. The sleeve may be open-ended, in which case it may extend from the needle hub over the sharpened end of the needle. Alternatively, the sleeve may be closed at one end, in which case it may cover only a portion of the needle.

Preferably, in the first condition of the resilient member with the sheath covering the needle, the sharpened end of the needle is spaced at least 1 mm from the opening in the end cap and the sheath extends at least 2 mm beyond the sharpened end of the needle.

In a particularly preferred arrangement, in the first condition of the resilient member with the sheath covering the needle, the sharpened end of the needle is spaced at least 2 mm from the opening in the end cap and the sheath extends at least 5 mm beyond the sharpened end of the needle.

The end cap may include a rigid blocking surface adjacent the opening through which the needle may pass, the blocking surface serving to contain the needle within the end cap.

In one arrangement, the end cap defines a recess for receiving the sharpened end of the needle and the opening comprises a passage extending from a leading end of the end cap into the recess adjacent the blocking surface.

Typically, the length of the passage is greater than the length of the portion of the sheath extending beyond the sharpened end of the needle. In this way, the sheath may be positioned entirely within the protective device.

In one arrangement, the opening in the end cap is located on one side of the cap, and the leading end of the end cap is inclined so as to extend backwards and away from the opening. In this way, with the resilient member in the first condition and the sheath removed from the needle, accidental contact with the inclined leading end of the end cap urges the sharpened end of the needle away from the opening in the end cap.

The resilient member may comprise a generally tubular member which defines at least one cut-out along its length for allowing the resilient member to deform between the first condition and the second condition.

Preferably, the at least one cut-out comprises a pair of opposed slits or slots which extend along a portion of the length of the resilient member to define two opposed limbs. The slits or slots may each include notches along their length which predispose the limbs to bow outwardly when the resilient member is deformed from the first condition to the second condition.

The resilient member may be mounted skew on the needle hub to provide the biasing of the end cap into the safety position.

The invention extends to a protective device of the type describe above attached to a needle assembly.

BRIEF DESCRIPTION OF THE DRAWINGS

The invention will now be described in more detail, by way of example only, with reference to the accompanying drawings in which:

FIG. 1 shows a cross-sectional view of a protective device for a needle assembly according to one embodiment of the present invention in an extended condition with a hypodermic needle inoperative prior to use;

FIG. 2 illustrates a top view in partial cross-section of the protective device of FIG. 1 in a withdrawn condition with the hypodermic needle still inoperative;

DETAILED DESCRIPTION OF THE INVENTION

Figure 5:
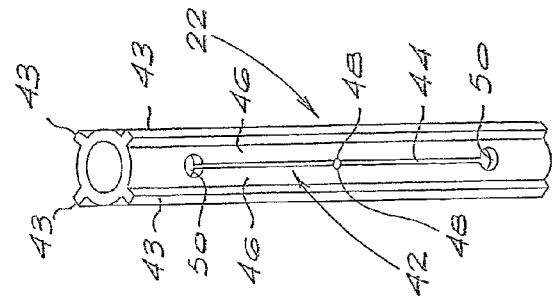
FIG. 5 illustrates a perspective view of a resilient member forming part of the protective device of the invention.

The present invention has application in the medical field, and more specifically in protective devices for hypodermic needles. The invention is embodied in a protective device for a needle assembly of the type generally used with syringes, catheters or blood-drawing holders. Such assemblies typically include a needle hub for attachment to the syringe, catheter or blood-drawing holder, and a hypodermic needle extending from the hub.

FIG. 1 of the accompanying drawings illustrates a protective device according to one embodiment of the present invention. The protective device is designated generally with the reference numeral 10 and is shown attached to a needle assembly 12 which includes a needle hub 14 and a hypodermic needle 16 extending from the hub to a sharpened end 18.

The needle protective device 10 includes an end cap 20, a resilient member 22 and a sheath 24. To protect users from the sharpened end of the needle 16, the end cap 20 is formed from a relatively rigid material. For example, the end cap may be injection moulded from a medical grade, clear polystyrene. As can be seen, the end cap 20 has a leading end 26, a trailing end 28 and a sidewall 30 extending between the leading end and the trailing end. The trailing end 28 defines a beveled entrance 32 feeding into a recess 34 for receiving the sharpened end 18 of the hypodermic needle. As representatively illustrated in FIG. 1, the end cap 20 defines an opening 36 adjacent a blocking surface 38. The opening 36 allows the needle 16 to pass through the end cap 20 for use, and the blocking surface 38 retains the sharpened end of the needle within the recess 34 after use, as will be described in more detail below.

With reference now to FIG. 5 of the drawings, the resilient member 22 may comprise a generally tubular member 42 which includes a pair of slits 44 (only one of which is visible) extending along a portion of the length of this member on opposite sides thereof to define a pair of resilient limbs 46. Each slit 44 may include a notch 48 on each side of the slit approximately midway along its length, and a generally circular opening 50 at each end of the slit, as shown. The notches 48 predispose the limbs 46 to bow outwardly in a manner which is described in more detail below, while the openings 50 prevent tearing at the ends of the slits 44 in use. As representatively illustrated in FIG. 5, the tubular member 42 may carry four, equally spaced apart fins 43 which extend along the length of this member for increased resiliency. The tubular member 42 may be formed in an injection moulding or extrusion process from a medical grade liquid or standard silicone rubber having a Shore hardness of 30 to 80.

With reference to FIGS. 1 and 2 of the drawings, the resilient member 22 may be attached to the needle hub 14 and to the end cap 20 by simply stretching the ends of the resilient member over the needle hub and the end cap. Alternatively, in addition to stretching, a suitable adhesive may be used to bond the resilient member 22 to the needle hub 14 and the end cap 20. A flange 40 on the end cap 20 and a flange 52 on the needle hub 14 serve as end stops during attachment of the resilient member to the needle hub and to the end cap, and the end of the resilient member 22 connected to the needle hub 14 is mounted skew, as shown most clearly in FIG. 1, so as to bias the end cap 20 in the direction of the arrow A.

The resilient member 22 is seen to extend about the needle 16 between the needle hub 14 and the end cap 20, and is deformable between a first condition in which it holds the end cap 20 over a sharpened end of the needle 16, as illustrated in FIG. 1, and a second condition in which the end cap 20 is withdrawn from the sharpened end of the needle 16, as illustrated in FIG. 2. This deformation is permitted by the resiliency of the limbs 46 which, under sufficient axial compressive loading, bow outwardly allowing the end cap 20 to be drawn back against the needle hub 14 into the FIG. 2 condition, and which, when released, have sufficient resiliency to return to the extended, FIG. 1 condition, snapping the end cap 20 over the sharpened end of the needle 16.

As representatively illustrated in FIG. 1 of the drawings, the sheath 24 may be formed as an open-ended sleeve which extends from the needle hub 14 beyond the sharpened end 18 of the needle. To protect users from the sharpened end of the needle prior to use, the open-ended sleeve may be formed from a relatively rigid material, such as, for example, a medical grade polypropylene, polystyrene or polyurethane.

The resilient member 22 is arranged to hold the end cap 20 over the sharpened end of the needle 16 so that the tip of the sharpened end falls short of the entrance to a passage 54 defining the opening 36 (see FIG. 1). Typically, the distance between the tip of the sharpened end 18 and the entrance to the passage 54 is at least 1 mm, and preferably is between 2 mm and 4 mm. The extent to which the sheath 24 extends beyond the tip of the sharpened end 18 depends on the nature and extent of the opening 36, but typically is at least 2 mm, and preferably is between 3 mm and 10 mm. In FIG. 1, it can be seen that the leading end of the sheath 24 extends into the passage 54 a sufficient distance to hold the sharpened end of the needle 16 in alignment with the opening 36, but not so far as to extend beyond the leading end 26 of the end cap 20.

Figure 3:
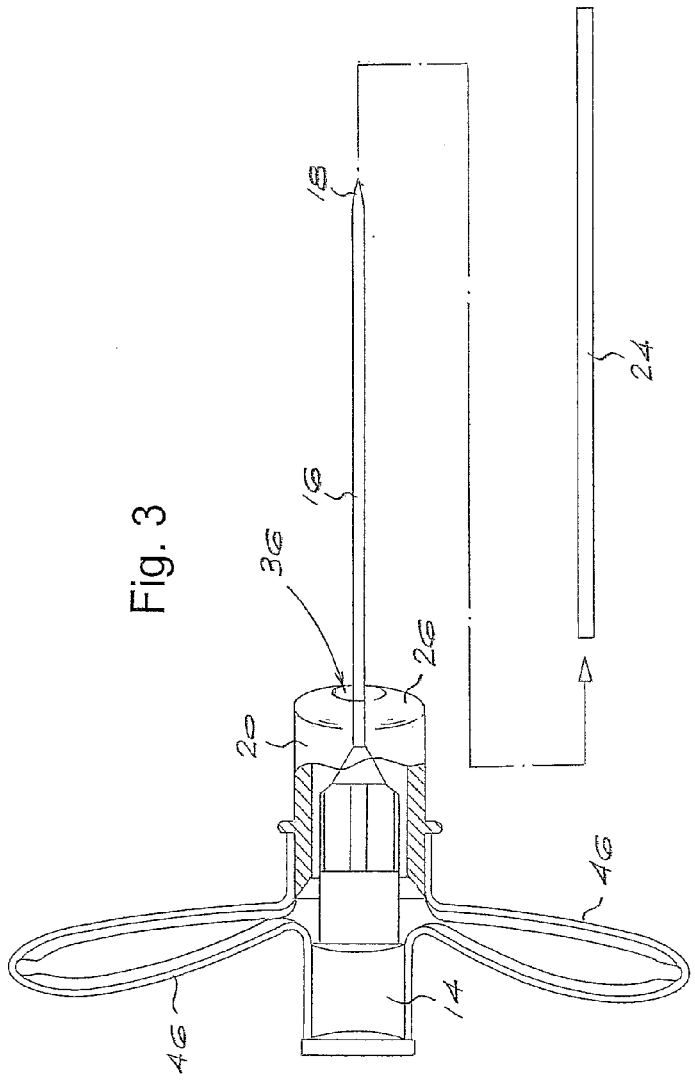
FIG. 3 illustrates a top view similar to that of FIG. 2 with the hypodermic needle exposed for use.

In practice, the needle hub 14 of the protective device 10 is connected to a syringe, a catheter or a blood-drawing holder (not shown) with the device in the FIG. 1 condition in which the sheath 24 aligns the needle 16 with the opening 36 in the end cap 20. In this condition, the sheath 24 is held in position by the biasing of the end cap 20 in the direction of the arrow A, and the rigidity of the sheath 24 prevents an accidental needle stick injury. To expose the needle 16 for use, the end cap 20 is simply withdrawn from the sharpened end of the needle 16 towards the needle hub 14 into the FIG. 2 condition, and the sheath 24 is removed, as illustrated in FIG. 3. With the end cap 20 withdrawn, the sheath 24 may be dropped off the needle 16 or alternatively removed by hand to expose the needle for use.

Figure 4:
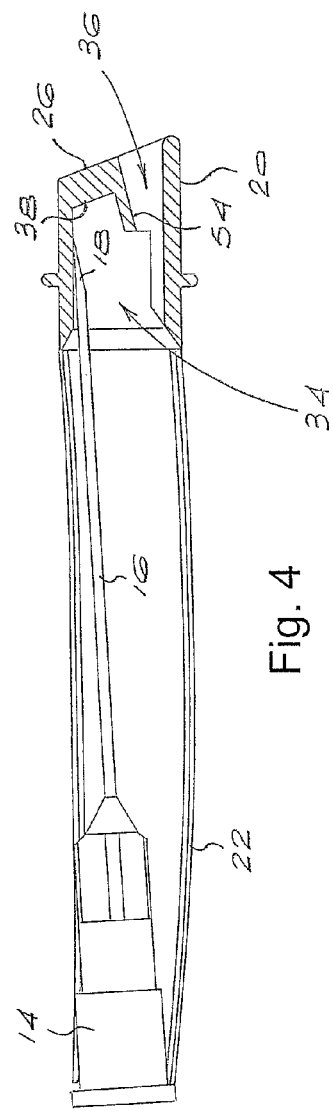
FIG. 4 illustrates a cross-sectional view of the protective device in an extended condition with the hypodermic needle inoperative after use.

After use, the end cap 20 is simply released, and the resiliency of the limbs 46 automatically drive the end cap 20 away from the needle hub 14 so that it snaps over the sharpened end of the needle 16, and the biasing of the end cap 20 by the resilient member 22 automatically moves the end cap into a safety position (illustrated in FIG. 4) in which the sharpened end of the needle 16 is located within the recess 34, offset relative to the opening 36 and aligned with the blocking surface 38. In this condition, the sharpened end of the needle 16 is safely retained within the end cap 20 during disposal of the needle arrangement, thereby reducing the likelihood of a needle stick injury. It will also be appreciated that in the event of accidental contact with the leading end of the end cap 20 after use, the inclined surface 26 serves to urge the sharpened end of the needle 16 away from the opening 36, thereby further reducing the likelihood of a needle stick injury.

Thus, the protective device 10 automatically retains the sharpened end of the needle 16 in a safe condition when the needle is not required, and yet allows the sharpened end to be exposed for use relatively easily.

The invention claimed is:

1. A protective device for a needle assembly having a needle hub and a needle projecting from the hub, the protective device comprising:
   an end cap which includes an opening through which the needle may pass;
   a resilient member extending about the needle between the needle hub and the end cap, the resilient member being deformable between a first condition in which it holds the end cap over a sharpened end of the needle and a second condition in which the end cap is withdrawn from the sharpened end of the needle, the resilient member being biased towards the first condition and being arranged to bias the end cap into a safety position in which the sharpened end of the needle is offset relative to the opening in the end cap; and
   a sheath, formed from a rigid material, covering at least the sharpened end of the needle, the sheath extending into or through the opening in the end cap so as to hold the sharpened end of the needle in alignment with the opening, against the bias of the end cap, and the sheath being removable from the needle to expose the sharpened end for use, and after use, to allow the resilient member, upon return to the first condition, to automatically displace the end cap into the safety position.

2. A protective device according to claim 1, wherein the sheath comprises a sleeve which extends over the sharpened end of the needle.

3. A protective device according to claim 2, wherein the sleeve is open-ended.

4. A protective device according to claim 3, wherein the sleeve extends from the needle hub over the sharpened end of the needle.

5. A protective device according to claim 2, wherein the sleeve is closed at one end.

6. A protective device according to claim 5, wherein the sleeve covers only a portion of the needle.

7. A protective device according to any one of claims 1 and 2-6, wherein, in the first condition of the resilient member with the sheath covering the needle, the sharpened end of the needle is spaced at least 1 mm from the opening in the end cap and the sheath extends at least 2 mm beyond the sharpened end of the needle.

8. A protective device according to any one of claims 1 and 2-6, wherein, in the first condition of the resilient member with the sheath covering the needle, the sharpened end of the needle is spaced at least 2 mm from the opening in the end cap and the sheath extends at least 5 mm beyond the sharpened end of the needle.

9. A protective device according to any one of claims 1 and 3-6, wherein the end cap includes a rigid blocking surface adjacent the opening through which the needle may pass, the blocking surface serving to contain the needle within the end cap.

10. A protective device according to claim 9, wherein the end cap defines a recess for receiving the sharpened end of the needle, and the opening comprises a passage extending from a leading end of the end cap into the recess adjacent the blocking surface.

11. A protective device according to claim 10, wherein the length of the passage is greater than the length of the portion of the sheath extending beyond the sharpened end of the needle.

12. A protective device according to any one of claims 1 and 2-6, wherein the opening in the end cap is located on one side of the cap, and the leading end of the end cap is inclined so as to extend backwards and away from the opening.

13. A protective device according to any one of claims 1 and 2-6, wherein the resilient member comprises a generally tubular member which defined at least one cut-out along its length for allowing the resilient member to deform between the first condition and the second condition.

14. A protective device according to claim 13, wherein the at least one cut-out comprises a pair of opposed slits or slots which extend along a portion of the length of the resilient member to define two opposed limbs.

15. A protective device according to claim 14, wherein the slits or slots each include notches along their length which predispose the limbs to bow outwardly when the resilient member is deformed from the first condition to the second condition.

16. A protective device according to any one of claims 1 and 2-6, wherein the resilient member is mounted skew on the needle hub to provide the biasing of the end cap into the safety position.

17. A protective device according to any one of claims 1 and 2-6 attached to a needle assembly which includes a needle hub and a hypodermic needle projecting from the hub.

* * * * *